US007858385B2

(12) United States Patent
Warner et al.

(10) Patent No.: US 7,858,385 B2
(45) Date of Patent: Dec. 28, 2010

(54) METHOD FOR DETECTING BINDING EVENTS USING MICRO-X-RAY FLUORESCENCE SPECTROMETRY

(75) Inventors: Benjamin P. Warner, Los Alamos, NM (US); George J. Havrilla, Los Alamos, NM (US); Grace Mann, Hong Kong (HK)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 09/859,701

(22) Filed: May 16, 2001

(65) Prior Publication Data

US 2003/0027129 A1 Feb. 6, 2003

(51) Int. Cl.
*G01N 21/76* (2006.01)
*G01N 33/543* (2006.01)
*G01N 33/00* (2006.01)

(52) U.S. Cl. .................. 436/172; 436/518; 436/103; 436/119; 436/124; 430/966

(58) Field of Classification Search ............... 436/518, 436/173, 172; 435/7.1, 174, 7.2
See application file for complete search history.

(56) References Cited

U.S. PATENT DOCUMENTS

| | | | | | |
|---|---|---|---|---|---|
| 4,436,826 | A | * | 3/1984 | Wang | 436/525 |
| 4,663,277 | A | * | 5/1987 | Wang | 435/5 |
| 4,830,192 | A | * | 5/1989 | Plester et al. | 209/3.1 |
| 5,143,854 | A | * | 9/1992 | Pirrung et al. | 436/518 |
| 5,324,633 | A | | 6/1994 | Fodor et al. | 435/6 |
| 5,547,839 | A | | 8/1996 | Dower et al. | 435/6 |
| 5,665,865 | A | * | 9/1997 | Lerner et al. | 530/387.3 |
| 5,733,731 | A | | 3/1998 | Schatz et al. | 435/6 |
| 5,902,723 | A | | 5/1999 | Dower et al. | 435/6 |
| 5,985,356 | A | | 11/1999 | Schultz et al. | 427/8 |
| 6,027,890 | A | | 2/2000 | Ness et al. | 435/6 |
| 6,030,917 | A | * | 2/2000 | Weinberg et al. | 502/104 |
| 6,034,775 | A | | 3/2000 | McFarland et al. | 356/364 |
| 6,041,095 | A | * | 3/2000 | Yokhin | 378/45 |
| 6,274,321 | B1 | * | 8/2001 | Blumberg | 435/6 |
| 6,391,590 | B1 | * | 5/2002 | Sano et al. | 435/69.7 |

FOREIGN PATENT DOCUMENTS

WO  WO 90/15070  * 12/1990
WO  WO9015070    12/1990

OTHER PUBLICATIONS

Goldin et al. "Quantitation of antibody binding to cell surface antigens by x-ray fluorescence spectrometry" Biochimica et biophysica acta, (Mar. 23, 1979) vol. 552, No. 1, pp. 120-128.*
Wielopolski et al. "Determination of ruthenium on DNA by XRF" Biological Trace Element Research (1987), 13, 283-90.*
Sigma-Aldrich (Product information sheet, Material Safety Data Sheet, and Safety Statements for cadmium chloride (catalog No. 28811), retrieved from http://www.sigmaaldrich.com/ on Apr. 23,2009.*
Francis A. Carey, "Organic Chemistry," McGraw-Hill Book Company, pp. 1086-1087.
J. M. Jaklevic et al., "X-Ray Fluorescence Analysis Applied to Small Samples," LBL-6451.
M. L. Rivers et al., "X-Ray Fluorescence Microscopy," BNL-44741, (1990).
E. D. Isaacs et al., "Synchrotron X-Ray Microbeam Diagnostics of Combinatorial Synthesis," Appl. Phys. Lett., vol. 73, No. 13, pp. 1820-1822 (1998).
Jenkins, "X-Ray Fluorescence Spectrometry," 2nd ed., John Wiley & sons, pp. 53-92 (1999).
Robert A. Carlton et al., "Qualitative Analysis of Solid Phase Synthesis Reaction Products by X-Ray Spectrometry," Microscopy and Microanalysis, vol. 3, No. 6, pp. 520-529 (1997).
J. P. Neilly et al., "Elemental Analysis of Individual Combinatorial Chemistry Library Members by Energy-Dispersive X-Ray Spectroscopy," Applied Spectroscopy, vol. 53, No. 1, pp. 74-81 (1999).
A. Berkessel et al., "Discovery of Peptide-Zirconium Complexes that Mediate Phosphate Hydrolysis by Batch Screening of a Combinatorial Undecapeptide Library," Angew. Chem. Ind. Ed, vol. 38, No. 1/2, pp. 102-105 (1999).

* cited by examiner

*Primary Examiner*—Gailene R Gabel
*Assistant Examiner*—Christine Foster
(74) *Attorney, Agent, or Firm*—Husch Blackwell LLP

(57) ABSTRACT

Method for detecting binding events using micro-X-ray fluorescence spectrometry. Receptors are exposed to at least one potential binder and arrayed on a substrate support. Each member of the array is exposed to X-ray radiation. The magnitude of a detectable X-ray fluorescence signal for at least one element can be used to determine whether a binding event between a binder and a receptor has occurred, and can provide information related to the extent of binding between the binder and receptor.

16 Claims, No Drawings

METHOD FOR DETECTING BINDING EVENTS USING MICRO-X-RAY FLUORESCENCE SPECTROMETRY

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to binding events and more particularly, to a method for detecting binding events between receptors arrayed onto a substrate and at least one potential binder using micro-X-ray fluorescence spectroscopy.

BACKGROUND OF THE INVENTION

The desire to hasten the identification of potentially important polymers, drugs, catalysts, ceramic superconductors, phosphors, chemical and biological sensors, and other materials is a constant challenge that has prompted the use of combinatorial synthetic and screening strategies for synthesizing these materials and screening them for desirable properties. Combinatorial synthesis involves assembling a "library", i.e. a very large number of chemically related compounds and mixtures, usually in the form of an array on a substrate surface. Combinatorial screening involves identifying which members of the array, if any, have the desirable property or properties. The array form facilitates the identification of a particular material on the substrate.

The synthesis of a surface-bound array of oligopeptides, short chain products of the condensation of amino acids, has been described in PCT Publication No. WO 90/15070 to M. C. Pirrung et al. entitled "Very Large Scale Immobilized Peptide Synthesis", incorporated herein by reference. Oligopepeptides were chosen because they exhibit the types of binding specificity of their longer-chain polypeptide counterparts, such as proteins. The chemical properties and in particular, the binding properties of a protein depend almost entirely on the exposed surface amino acid residues of the polypeptide chain. These residues can form weak noncovalent bonds with other molecules. An effective binding between the protein, one example of a group of materials herein referred to as "receptors", and the material that binds to the receptor, referred to herein as "binder", generally requires that many weak bonds form simultaneously between the protein receptor and the binder. Binders include organic molecules, inorganic molecules, salts, metal ions, and the like. The bonds between the protein and the binder form at the "binding site" of the protein. The binding site is usually a cavity in the protein that is formed by a specific arrangement of amino acids that often belong to widely separated regions of the polypeptide chain and represent only a minor fraction of the total number of amino acids present in the chain. Binders must fit precisely into the binding site for effective binding to occur. The shape of these binding sites can differ greatly among different proteins, and even among different conformations of the same protein. Even slightly different conformations of the same protein may differ greatly in their binding abilities. For further discussion of the structure and function of proteins, see: Bruce Alberts et al., "Molecular Biology of the Cell", $2^{nd}$ edition, Garland Publishing, Inc., New York, 1989; and H. Lodish et al., "Molecular Cell Biology", $4^{th}$ edition, W. H. Freeman and Company, 2000.

After a receptor array is prepared, it is screened to determine which members have the desirable property or properties. U.S. Pat. No. 5,143,854 to M. C. Pirrung et al. entitled "Large Scale Photolithographic Solid Phase Synthesis of Polypeptides and Receptor Binding Screening Thereof", which issued Sep. 1, 1992, hereby incorporated by reference, describes one such screening method. A polypeptide array is exposed to a ligand (an example of a binder) to determine which members of the array bind to the ligand. The ligands described are radioactive, or are "tagged", i.e. attached via one or more chemical bonds to a chemical portion that fluoresces when exposed to non-ionizing, ultraviolet radiation. Thus, the attached portion, i.e. the tag, makes the binder visible by interrogation with ultraviolet radiation. Tagged molecules have also been used to aid in sequencing immobilized polypeptides as described, for example, in U.S. Pat. No. 5,902,723 to W. J. Dower et al. entitled "Analysis of Surface Immobilized Polymers Utilizing Microfluorescence Detection," which issued May 11, 1999. Immobilized polypeptides are exposed to molecules labeled with fluorescent tags. The tagged molecules bind to the terminal monomer of a polypeptide, which is then cleaved and its identity determined. The process is repeated to determine the complete sequence of the polypeptide.

It is generally assumed that the attachment of a fluorescent tag to a potential binder only serves to make visible the otherwise invisible potential binder, and does not alter its binding properties. Since it is well known that even small changes to the structure of a molecule could affect its function, this assumption that a tagged binder, i.e. a "surrogate", has the same binding affinity as the untagged binder may not be a valid one. Small structural changes that accompany even a conformational change of a receptor have been known to affect the binding affinity of the receptor. The tagged surrogates are structurally different from their untagged counterparts, and these structural differences could affect their binding affinities. Since binding affinities derived using tagged surrogates are suspect, the binding properties of receptors and binders should be evaluated using the untagged binder or receptor and not with a tagged surrogate.

Therefore, an object of the present invention is to provide an efficient, combinatorial method of evaluating the binding properties of untagged potential binders with receptors.

Another object of the present invention is to provide a combinatorial screening method for directly comparing the binding properties of receptors/binders with their tagged surrogates.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a method for detecting a binding event between at least one binder and members of a receptor array. The method comprises the steps of exposing a plurality of receptors to at least one potential binder; arraying the receptors onto a substrate; exposing each member of the array that has already been exposed to potential binders to X-ray radiation to induce an X-ray fluorescence signal from each member of the array now bound to at least one binder, thereby indicating that a binding event has occurred; and detecting an X-ray fluorescence signal resulting from exposure to the X-ray radiation from any member of the array where a binding event has occurred.

DETAILED DESCRIPTION OF THE INVENTION

Briefly, the invention includes a method for detecting a binding event between members of a surface-bound receptor array and at least one potential binder using micro-X-ray fluorescence spectroscopy. A plurality of bead-supported receptors were exposed to at least one potential binder for a period of time sufficient for binding to occur, and then immobilized as an array onto a surface. Each member of the array was exposed to X-ray radiation. The detection of an X-ray fluorescence signal from a member of the array indicated that a binding event had occurred between that receptor and a binder. The intensity of the signal indicated the extent of the binding event, and could also be used to determine the binding affinity of the receptor to the binder.

The method of the invention uses X-ray fluorescence as a probe to detect binding events. X-ray fluorescence spectrometry is a powerful spectroscopic technique that has been used to determine the chemical elements that are present in a chemical sample, and to determine the quantity of those elements in the sample. The underlying physical principle of the method is that when an atom of a particular element is irradiated with X-ray radiation, the atom ejects a core electron such as a K shell electron. The resulting atom is in an excited state, and it can return to the ground state by replacing the ejected electron with an electron from a higher energy orbital. This is accompanied by the emission of a photon, i.e. X-ray fluorescence, and the photon energy is equal to the difference in the energies of the two electrons. Each element has a characteristic set of orbital energies and therefore, a characteristic X-ray fluorescence spectrum.

An X-ray fluorescence spectrometer is an apparatus capable of irradiating a sample with an X-ray beam, detecting the X-ray fluorescence from the sample, and using the X-ray fluorescence to determine which elements are present in the sample and providing the quantity of these elements. The X-ray fluorescence spectrometer used to demonstrate the invention was the commercially available EDAX Eagle XPL energy dispersive X-ray fluorescence spectrometer, equipped with a microfocus X-ray tube, lithium drifted silicon solid state detector, processing electronics, and vendor supplied operating software. The EDAX Eagle XPL spectrometer can be used to determine the quantity in a sample of any element with an atomic number equal to or greater than the atomic number of sodium (sodium has atomic number 11). The vendor software used to operate the spectrometer allowed the simultaneous quantitation of 15 different elements for each member of the array.

The method of the present invention was demonstrated with a polymer bead-supported oligopeptide library purchased from Biopeptide Co., a commercial vendor. The library consisted of 625 unique 11-mer oligopeptides, i.e. each oligopeptide had a unique sequence of 11 amino acids. The oligopeptides used had the following general formula: XaaGlyGlyXaaGlyGlyXaaGlyGlyXaaPhe (SEQ ID NO:1). In this formula, the phenylalanine (Phe) amino acid of the oligopeptide is chemically bonded to the polymer bead support. The abbreviations for the amino acids in this formula are standard three-letter abbreviations used for the α-amino acids found in proteins and can be found in many textbooks (for example, see table 29.1 in F. A. Carey, Organic Chemistry, McGraw-Hill, 1987, pp. 1086-1087). In the formula: Phe is phenylalanine; Gly is glycine, and Xaa is any one of the following five amino acids: histidine (His); arginine (Arg); serine (Ser); tryptophan (Trp); and tyrosine (Tyr). Permutation of these amino acids among the four 'X' positions generates a library of 625 unique 11-mer oligopeptides.

The bead support was a polymer made from Wang polystyrene resin. About 2 micrograms (μg) of each unique oligopeptide (corresponding to about 0.06 nanomoles, nmol) was supported on each bead. That is, each bead contains only one kind of 11-mer oligopeptide. The beads were about 80-120 micrometers in diameter, with an average diameter of about 100 micrometers.

The array format facilitated the identification of the particular oligopeptide-supported beads that exhibited the most significant X-ray fluorescence and therefore, the strongest binding effects. Once identified, these beads were then removed from the array and the amino acid sequence of the bound oligopeptides was determined by Edman degradation analysis. These oligopeptides were also characterized by MALDI-TOF MS, a mass spectroscopic technique. All other reagents used were commercially available and used without further purification.

The exposure of bead-supported receptors to potential binders such as organophosphates, organosulfonates, halides, metals, and the like, generally involved incubating the library of beads in an aqueous solution (pH 5.2-5.6) containing potential binder (about 0.5-100 μmol) for about 5-48 h at room temperature. In some cases, multiple treatments with a binder or binders resulted in an enhanced binding effect. After the incubation period, the beads were removed from the solution, washed with copious amounts of water, air-dried, and immobilized either on glass microscope slides with double-stick tape, or on Tacky Dot™ plates, to provide an oligopeptide receptor array. Tacky Dot™ plates have arrays of adhesive dots on the surface and were used without any chemical modification. An X-ray fluorescence spectrometer was then used to determine which beads of the array had a measurable amount of binder attached. Each member of the array was exposed to spatially restricted X-ray radiation of a nominal beam size of 50 micrometers, and the X-ray fluorescence of particular elements were detected and quantified. If, for example, an organophosphate was tested as a potential binder, the element phosphorus was chosen as a detected element. For potential organosulfonate binders, sulfur was chosen. For potential halide binders (as halogenated organic molecules), the particular halides (bromide for brominated organic compounds, chloride for chlorinated organic compounds, etc.) were chosen. For potential metal ion binders, the particular metal ion was chosen, etc. The X-ray fluorescence intensity was used to detect a binding event, and can also be used to determine the binding affinity of the binder to the receptor. The amount of receptor present on a bead can be verified from the X-ray fluorescence of the oligopeptide-supported bead prior to incubation in the binder solution. Quantification of the binder content was used to determine which of the substrate bound oligopeptide receptors were the most efficient receptors for binding a particular binder.

Particular examples of phosphates and phosphonic acids that were tested as potential binders included 4-chloro-5-bromo-indolyl phosphate, diethyl thiophosphate, diethyl dithiophosphate, diethyl cyanophosphonate, and methylphosphonic acid. Examples of organosulfates, sulfonic acids, and sulfides that were tested as binders include indolyl-sulfate, hydroxyethyl-piperazinepropanesulfonic acid, toluenesulfonic acid, L-cysteine, and N,N-diethylaminoethanethiol. Halide in the form of hydrogen chloride was also tested as a binder. Metal ions, in the form of soluble halide and nitrate salts, were also tested as binders; those tested include the following: $ZrCl_4$, $La(NO_3)_3$, $Ce(NO_3)_3$, $Pr(NO_3)_3$, $Nd(NO_3)_3$, $Sm(NO_3)_3$, $Eu(NO_3)_3$, $Gd(NO_3)_3$, $Tb(NO_3)_3$, $Dy(NO_3)_3$, $Ho(NO_3)_3$, $Er(NO_3)_3$, $Tm(NO_3)_3$, $Yb(NO_3)_3$, and $Lu(NO_3)_3$.

The method of the invention, in particular, was used to detect binding of N,N-diethylaminoethanethiol and/or methylphosphonic acid with members of the 11-mer oligopeptide library. An aqueous solution of these materials was prepared by combining 0.2 mL of a 200 mM solution of methylphosphonic acid (40 μmol) with 0.2 mL of a 210 mM solution of the hydrogen chloride salt of N,N-diethylaminoethanethiol (42 μmol). About 2500 of the oligopeptide-supported beads (corresponding to 5 mg total weight with about 1.6 μmol total oligopeptide) were incubated in the solution at room temperature for 2 days. The beads were then removed from solution, washed with 10 mL of water, air dried, and immobilized on a Tacky Dot™ plate as an array. The beads of the array were then analyzed for binding using micro-X-ray fluorescence spectrometry using the EDAX micro-fluorescence instrument. Two beads in particular displayed a strong binding effect with methylphosphonic acid. Their amino acid sequences, as determined by Edman degradation analysis, were the following (the amine end group belongs to the amino acid at the end of the chain): 1) HisGlyGlyHisGlyGlyHisGlyGlyArgPhe (SEQ ID NO:2); and 2) TyrGlyGlyTyrGlyGlyTrpGlyGlyTyrPhe (SEQ ID NO:3). Two different beads displayed a strong binding effect with the thiol. Their amino acid sequences, as determined by Edman degradation analysis, were the following: 3) SerGlyGlyArgGlyGlyHisGlyGlyHisPhe (SEQ ID NO:4); and 4) TrpGlyGlyHisGlyGlyHisGlyGlyTrpPhe (SEQ ID NO:5).

The invention was also used to screen potential metal catalyst binders. The chemical procedure employed was similar to one described by A. Berkessel and D. A. Herault in "Discovery of Peptide-Zirconium Complexes That Mediate Phosphate Hydrolysis by Batch Screening of a Combinatorial Undecapeptide Library", Angew. Chem.-Int. Ed. 1999, vol. 38, p. 102, hereby incorporated by reference. Berkessel et al. exposed a combinatorial array of bead-supported oligopeptides to zirconium tetrachloride. The resulting zirconium complex binds to some of the peptides, and some of the peptides with bound zirconium catalyze the hydrolytic cleavage of a phosphate ester. The catalytic activity of each exposed bead was determined by exposure to 4-chloro-5-bromo-indolyl phosphate, which undergoes phosphate ester cleavage to form 4-chloro-5-bromo-indoxyl and rapidly oxidizes to 4,4'-dichloro-5,5'-dibromo-indigo, an insoluble blue dye. The relative intensity of the blue color indicates the relative amount of blue dye for a particular bead, and was assumed to be proportional to the activity of the catalyst on that bead; a more intensely blue colored bead indicates a more active catalyst.

With regard to an example of the present invention, about 12,500 oligopeptide-supported beads weighing a total of about 25 milligrams, corresponding to about 8.2 total micromoles of oligopeptide, were pretreated by incubation in a room-temperature, aqueous solution of zirconium tetrachloride, $ZrCl_4$ (4.0 mg, 17 μmol in 0.6 mL water), for about 3 days. The beads were removed from solution, washed with about 10 mL of water, and air-dried. A solution of EPPS buffer (EPPS=hydroxyethyl-piperazinepropanesulfonic acid) at a pH of 5.3 was prepared. A buffered solution was prepared by combining about 0.3 mL of a 320 millimolar (mM) solution of the EPPS buffer solution with 0.3 mL of a 5.4 millimolar (mM) solution of 4-chloro-5-bromo-indolyl phosphate (about 1.6 μmol) and 0.3 mL of a 8.6 mM solution of zirconium tetrachloride (about 2.6 μmol). About 2600 of the pretreated beads, weighing 5.3 mg were incubated in the buffered solution at room temperature for about 15 h. They were removed from the buffered solution, washed with about 10 mL water, air dried, and immobilized on a Tacky Dot™ plate in the form of an array. Each member of the array was analyzed by X-ray fluorescence spectrometry. The Tacky Dot™ plate was placed in the EDAX MXRF instrument under vacuum. The instrument was operated at 35 kV and 500 μA using a rhodium X-ray tube. The area scanned was 14×7.4 mm using a step size of 27 μm in the x-direction and 19 μm in the y-direction. The pixel area was 512×400 with a 200 μsec dwell time per point. The point spectra were acquired with an acquisition time of 100 live seconds, the amount of time that the detector is actively obtaining counts. The single point spectra provided the elemental intensities for the beads, several of which are listed in the Table below.

TABLE

| Bead | Color | Zr (counts) | Br (counts) | Br/Zr | P (counts) |
|---|---|---|---|---|---|
| 1 | Yellow | 93.68 | 303.49 | 3.24 | 545 |
| 2 | Amber | 34.92 | 118.74 | 3.40 | 82.21 |
| 3 | Clear | 13.75 | 115.2 | 8.38 | 184.41 |
| 4 | Dark gray/blue | 7.92 | 299.68 | 37.84 | 104.29 |
| 5 | Yellow | 37.69 | 330.98 | 8.78 | 264.62 |
| 6 | Dark yellow | 4 | 157.93 | 39.48 | 50.16 |
| 7 | Clear | 6.06 | 131.88 | 21.76 | 32.21 |
| 8 | Gray | 0 | 81.9 | 0.00 | 29.72 |
| 9 | Dark yellow | 10.27 | 262.58 | 25.57 | 116.86 |
| 10 | Gray/blue | 19.56 | 105.71 | 5.40 | 21.87 |
| 11 | Yellow | 15.56 | 259.2 | 16.66 | 191.59 |
| 12 | Yellow | 11.35 | 241.71 | 21.30 | 79.2 |
| 13 | Blue/gray | 47.93 | 276.95 | 5.78 | 86.24 |
| 14 | Clear | 15.12 | 178.57 | 11.81 | 185.84 |
| 15 | Yellow | 11.15 | 119.19 | 10.69 | 100.88 |

The most effective bead-supported catalyst produces the most product per unit of catalyst, and is a blue colored bead with a high Br count and a low P count and large Br/Zr ratio. Of the fifteen beads listed in the above Table, bead 4 includes all of these features. Blue beads 10 and 13 have significantly smaller Zr/Br ratios than bead 4, indicating poorer catalyst activity. In addition, those beads with a high Zr content bind strongly to Zr, indicating that the corresponding oligopeptides could be used as a separation agent specific for Zr. Analysis by MALDI-TOF Mass spectrometry, or by Edman degradation as previously described, can provide the amino acid sequences for the oligopeptides.

The examples described involve monitoring the elements P, Br, and S, which are present in the binder but not in any of the receptors. The X-ray fluorescence signal due to these elements indicates that the particular binder with these elements is present, making the determination of a binding effect straightforward. It should be understood that the X-ray fluorescence spectrometer can determine whether a particular element is present and also the quantity of that element. Therefore, the analysis may include a determination of the quantity of an element common to both the binder and the receptor. If a binding event occurs between a binder and receptor, and both the binder and receptor include the elements carbon and oxygen, for example, an X-ray spectrometer capable of analyzing for these elements can distinguish between the amount of these elements present in the receptor and the amount present in a binder-receptor complex. For binders that only include elements that are also common to the receptor, the difference in the signal intensity between the receptor and the binder-receptor complex for these elements provides an indication that a binding event has occurred.

Other metal ions, purchased as standard ICP solutions (100 µg/mL in 2% $HNO_3$), were also tested as binders; they include ions of Be, Ca, Cd, Co, Cr, Cu, Fe, Li, Mg, Mn, Mo, Ni, Pb, Sb, Se, Sr, Ti, TI, V, and Zn. Metal ions of Ce, Ag, Ba and Hg, available as a standard solution, 1000 µg/mL in 2% $HNO_3$ solution, were also tested as potential binders.

Oligopeptides are only one type of receptor that can be used with the present invention, and clearly many other types of receptors can also be used. Esters, amines, imines, aldehydes, ketones, amides, ethers, olefins, halogenated organic molecules, antibodies, drugs, steroids, amino acids, and nucleotides can be used. Other types of oligomers such as oligonucleotides, oligosaccharides, and oligopeptides can be used. Polymers such as polyolefins, polyurethanes, polyesters, polycarbonates, polyamines, polyamides, halogenated polymers, polypeptides, polynucleotides, and polysaccharides, and nucleic acids, to name a few, can also be used as receptors. Both naturally occurring and man-made materials can be used. Also, complex structures of molecules can be used as receptors that include cell membrane receptors, viruses, cells, cellular membranes, organelles, and the like.

Similarly, many different materials can be tested as potential binders. These materials include organic molecules such as esters, amines, imines, aldehydes, ketones, amides, ethers, olefins, and halogenated organic molecules. Antibodies, drugs, hormones (e.g. steroids and the like), amino acids, and nucleic acids can also be tested as potential binders. Oligomers such as oligonucleotides, oligosaccharides, and oligopeptides, and polymers such as polyolefins, polyurethanes, polyesters, polycarbonates, polyamines, polyamides, halogenated polymers, polypeptides, polynucleotides, polysaccharides, nucleic acids, to name a few, can be also be tested as binders.

Both naturally occurring and man-made materials can be used as binders. Metal ions such as calcium ion, barium ion, sodium ion, potassium ion, iron ion, palladium ion, silver ion, and strontium ion can be used. Anions such as bromide, chloride, iodide, sulfide, and selenide, for example, can be tested as potential binders. Complex ions such as oxyanions, polyoxoanions, phosphate, organophosphates, sulfate, organosulfates, zirconate, molybdate, tungstate, chromate, for example, can be tested. Also, agonists and antagonists for cell membrane receptors, toxins, enzymes, enzyme substrates, cofactors, and monoclonal antibodies can also be tested.

The invention can also be used to determine the binding affinity (BA) between a binder and a receptor. The BA is defined as the concentration of the binder-receptor complex divided by the product of the concentrations of the binder and the receptor. To determine the binding affinity (BA), the concentrations of the binder and receptor, and the concentration of the binder-receptor complex must be determined. There are several ways, both non-destructive and destructive (e.g. removal of the receptor from the support bead), of determining the concentration of the receptor. The concentration of the receptor can be determined directly and non-destructively (i.e. the receptor remaining on the bead) by a spectroscopic technique such as by X-ray fluorescence. The receptors can also be cleaved from the bead, collected, and quantified using high performance liquid chromatography. The concentration of the receptor can also be estimated indirectly from parameters related to the support beads, such as the size and surface area of the beads.

Similarly, the concentration of the binder can be determined by quantifying the amount of binder remaining in solution after the bead-supported receptors have been submerged in the binder solution for the time period allowed for binding to occur.

It is generally assumed, particularly in the development of new catalysts on ligand (e.g. a peptide ligand) coated beads, that the distribution of ligand on each bead is similar. This often unstated assumption is illustrated by the methods used to determine catalyst efficiency. These methods as exemplified in the aforementioned Berkessel et al. publication rely on quantifying the product of the catalytic reaction without quantifying the amount of catalyst that is formed. Product quantification methods that ignore the quantification of the catalyst lead to faulty conclusions about catalyst efficiency since catalyst efficiencies cannot be determined without knowledge of the quantity of the catalysticatalysts used.

The present invention uses micro-X-ray fluorescence to determine the presence and relative amounts of elements. These elements can be in the form of metal ions such as calcium ion, chloride, bromide, iodide, phosphorus, and sulfur, the latter two being important constituents of polypeptides such as enzymes, RNA, and DNA. Thus, the invention provides a non-destructive method of screening the binding of a receptor array to a potential binder, and for quantifying the binding affinity. A commercially available micro-X-ray fluorescence spectrometer has been used to evaluate the binding of materials to an array of oligopeptides, each oligopeptide bound to a polystyrene bead substrate.

In summary, the present invention provides a method for detecting binding events between arrayed receptors and potential binders. The invention provides significant advantages over known methods for measuring binding affinities since known methods often require either radioactive binders, or binders that include a covalently attached label that fluoresces upon exposure to ultraviolet excitation radiation. Since the invention does not require radioactive or chemically tagged materials, the problems dealing with handling of radioactive materials and the disposal of radioactively contaminated waste are avoided. Importantly, since the use of artificially tagged materials is not required, there can be no interference from the tag in the evaluation of the binding affinity of the corresponding desired untagged material. Further, in contrast to methods that require tags, the method of the present invention can be used to evaluate the binding affinity of materials that do not fluoresce while exposed to ultraviolet radiation. It should be understood that although tagged materials are not required, they could also be used and this aspect of the invention offers a distinct advantage in that the invention can provide a direct comparison of binding affinity of the untagged binder with that of the corresponding tagged surrogate. This comparison could validate or invalidate the assumption that a particular untagged binder and its tagged surrogate have the same binding affinity to a particular substrate.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detecting a binding event between at least one binder and members of a receptor array, comprising the steps of:
   (a) exposing a plurality of bead-supported and nonradioactive receptors to at least one binder having a chemically associated and nonradioactive element detectable by X-ray fluorescence to form at least one bound, bead-supported receptor-binder complex; wherein the element is selected from the group consisting of P, S, and Br; and wherein the binder is selected from the group consisting of esters, amines, imines, aldehydes, ketones, amides, ethers, olefins, halogenated organic molecules, antibodies, drugs, hormones, steroids, amino acids, nucleic acids, oligomers, oligonucleotides, oligosaccharides, oligopeptides, polyolefins, polyurethanes, polyesters, polycarbonates, polyamines, polyamides, halogenated polymers, polypeptides, polynucleotides, polysaccharides, anions, complex ions, oxoanions, polyoxoanions, phosphate, organophosphates, sulfate, organosulfates, zirconate, agonists and antagonists for cell membrane receptors, toxins, enzymes, enzyme substrates, cofactors, and antibodies;
   (b) washing said bound, bead-supported receptor-binder complex to remove unbound binder from said bound, bead-supported receptor-binder complex;
   (c) arraying said bound, bead-supported receptor-binder complex onto a substrate; and
   (d) detecting a binding event by exposing said bound, bead-supported receptor-binder complex to X-ray radiation in order to generate an X-ray fluorescence signal from said detectable element in said bound, bead-supported receptor-binder complex.

2. The method of claim 1, wherein the receptor comprises at least one organic compound.

3. The method of claim 1, wherein the receptor comprises at least one oligomer.

4. The method of claim 1, wherein the receptor comprises at least one polymer.

5. The method of claim 1, wherein the receptor is selected from the group consisting of esters, amines, imines, aldehydes, ketones, amides, ethers, olefins, halogenated organic molecules, antibodies, drugs, steroids, amino acids, nucleic acids, oligomers, oligonucleotides, oligosaccharides, oligopeptides, polyolefins, polyurethanes, polyesters, polycarbonates, polyamines, polyamides, halogenated polymers, polypeptides, polynucleotides, polysaccharides, cell membrane receptors, viruses, cells, cellular membranes, and organelles.

6. The method of claim 1, wherein the binder comprises at least one organic molecule.

7. The method of claim 1, wherein the binder comprises at least one oligomer.

8. The method of claim 1, wherein the binder comprises at least one polymer.

9. A method for detecting chemical binding between at least one binder and members of a receptor array, comprising the steps of:
   (a) exposing a plurality of bead-supported and nonradioactive receptors to at least one untagged binder having a chemically associated and nonradioactive element detectable by X-ray fluorescence to form at least one bound, bead-supported receptor; wherein the element is selected from the group consisting of P, S, and Br; and wherein the binder is selected from the group consisting of esters, amines, imines, aldehydes, ketones, amides, ethers, olefins, halogenated organic molecules, antibodies, drugs, hormones, steroids, amino acids, nucleic acids, oligomers, oligonucleotides, oligosaccharides, oligopeptides, polyolefins, polyurethanes, polyesters, polycarbonates, polyamines, polyamides, halogenated polymers, polypeptides, polynucleotides, polysaccharides, anions, complex ions, oxoanions, polyoxoanions, phosphate, organophosphates, sulfate, organosulfates, zirconate, agonists and antagonists for cell membrane receptors, toxins, enzymes, enzyme substrates, cofactors, and antibodies;
   (b) washing said bound, bead-supported receptor;
   (c) arraying said bound, bead-supported receptor onto a substrate; and
   (d) detecting an X-ray fluorescence signal generated by said detectable element in said bound, bead-supported receptor.

10. The method of claim 9, wherein the receptor comprises at least one organic compound.

11. The method of claim 9, wherein the receptor comprises at least one oligomer.

12. The method of claim 9, wherein the receptor comprises at least one polymer.

13. The method of claim 9, wherein the receptor is selected from the group consisting of esters, amines, imines, aldehydes, ketones, amides, ethers, olefins, halogenated organic molecules, antibodies, drugs, steroids, amino acids, nucleic acids, polyurethanes, polyesters, polycarbonates, polyamines, polyamides, halogenated polymers, polypeptides, polynucleotides, polysaccharides, cell membrane receptors, viruses, cells, cellular membranes, and organelles.

14. The method of claim 9, wherein the binder comprises at least one organic molecule.

15. The method of claim 9, wherein the binder comprises at least one oligomer.

16. The method of claim 9, wherein the binder comprises at least one polymer.

* * * * *

```
                              SEQUENCE LISTING

<160> NUMBER OF SEQ ID NOS: 5

<210> SEQ ID NO 1
<211> LENGTH: 11
<212> TYPE: PRT
<213> ORGANISM: artificial sequence
<220> FEATURE:
<223> OTHER INFORMATION: artificial sequence is synthesized
<220> FEATURE:
<221> NAME/KEY: MISC_FEATURE
<222> LOCATION: (1)..(11)
<223> OTHER INFORMATION: X can be H, R, S, W, or Y

<400> SEQUENCE: 1

Xaa Gly Gly Xaa Gly Gly Xaa Gly Gly Xaa Phe
1               5                   10

<210> SEQ ID NO 2
<211> LENGTH: 11
<212> TYPE: PRT
<213> ORGANISM: artificial sequence
<220> FEATURE:
<223> OTHER INFORMATION: artificial sequence is synthesized

<400> SEQUENCE: 2

His Gly Gly His Gly Gly His Gly Gly Arg Phe
1               5                   10

<210> SEQ ID NO 3
<211> LENGTH: 11
<212> TYPE: PRT
<213> ORGANISM: artificial sequence
<220> FEATURE:
<223> OTHER INFORMATION: artificial sequence is synthesized

<400> SEQUENCE: 3

Tyr Gly Gly Tyr Gly Gly Trp Gly Gly Tyr Phe
1               5                   10

<210> SEQ ID NO 4
<211> LENGTH: 11
<212> TYPE: PRT
<213> ORGANISM: artificial sequence
<220> FEATURE:
<223> OTHER INFORMATION: artificial sequence is synthesized

<400> SEQUENCE: 4

Ser Gly Gly Arg Gly Gly His Gly Gly His Phe
1               5                   10

<210> SEQ ID NO 5
<211> LENGTH: 11
<212> TYPE: PRT
<213> ORGANISM: artificial sequence
<220> FEATURE:
<223> OTHER INFORMATION: artificial sequence is synthesized

<400> SEQUENCE: 5

Trp Phe Phe His Gly Gly His Gly Gly Trp Phe
1               5                   10
```